US00PP16634P3

(12) United States Plant Patent
Miyazaki

(10) Patent No.: US PP16,634 P3
(45) Date of Patent: Jun. 13, 2006

(54) ***SENECIO* PLANT NAMED 'SUNSENEBARE'**

(50) Latin Name: ***Senecio cruentus*×*Senecio heritieri***
Varietal Denomination: Sunsenebare

(75) Inventor: Kiyoshi Miyazaki, Hikone (JP)

(73) Assignee: Suntory Flowers Limited, Tokyo (JP)

( * ) Notice: Subject to any disclaimer, the term of this patent is extended or adjusted under 35 U.S.C. 154(b) by 73 days.

(21) Appl. No.: 10/815,180

(22) Filed: Mar. 31, 2004

(65) Prior Publication Data

US 2005/0223451 P1 Oct. 6, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP12,162 P2 10/2001 Miyazaki

FOREIGN PATENT DOCUMENTS

JP PBR 10502 9/2002

OTHER PUBLICATIONS http://www.yourdictionary.com "capitula".*
http://glossary.gardenweb.com "capitulum".*
Flower & Green autumn and winter Catalog 2004, Suntory Flowers, Ltd., (3 pp), Published 2003, with brief English explanation and partial translation of p. 3.
Suntory Collection 2004, Moerheim New Plant bv, (3 pp), Published 2003 with English translation of p. 75.
The Catalog for Gardening Farm, '94 autumn–'95 spring, Sakata seed Co., (3 pp), Published 1994 with brief English translation of p. 43.
The Plant Finder, 1994/95 Edition, Royal Horticultural Society, (4 pp), Published 1994.
Explanation of Publication of Japanese PBR Registration and family documents therein.

* cited by examiner

*Primary Examiner*—Kent Bell
*Assistant Examiner*—Louanne Krawczewicz Myers
(74) *Attorney, Agent, or Firm*—Christie, Parker and Hale, LLP

(57) ABSTRACT

Disclosed herein is a new variety of *Senecio* plant having a semi-dwarf, obconical shaped with abundant branching and small leaves. The capitula are single and small, the ray florets and the disc florets having vivid reddish purple color. The blooming time is early and flowering duration is longer than *Senecio cruentus*. 'Sunsenebare' has low fertility.

2 Drawing Sheets

Botanical classification: *Senecio cruentus*×*Senecio heritieri.*
Varietal denomination Sunsenebare.

BACKGROUND OF THE VARIETY

The present invention relates to a new variety of *Senecio* plant, which originated from the crossing of the *Senecio cruentus* cultivar 'Extra Rose' (unpatented) as the female parent and a variety of *Senecio heritieri* as the male parent.

There are many varieties in *Senecio* cultivated in the world. Many of these cultivated varieties have capitula of a single color of white, pink red, blue or violet, while others have marginal variegation with off color parts.

The female parent 'Extra Rose' used in the crossing which produced 'Sunsenebare' is a cultiver of *Senecio cruentus.* It is Early flowering variety having a dwarf and mounding shape with large leaves. It has small single capitula, the ray florets having a vivid purplish red color. The seed of 'Extra Rose' is commercially available.

The male parent used in the crossing which produced 'Sunsenebare' is a cultivar of *Senecio heritieri,* having a high and dome-shaped growth habit with abundant branching and small leaves. It has small single capitula, the ray florets having strong purple with vague white center coloration. *Senecio heritieri* was introduced into the United States from nurseries in England and, to Applicant's knowledge, has no variety name and is patented nor sold in the United States.

In January 1996, a crossing of 'Extra Rose' as the female parent and *Senecio heritieri* as the male parent was conducted at Hakushu-cho, Kitakoma-gun, Yamanashi-ken, Japan. The seedlings obtained from that crossing were grown in pots in glasshouses and evaluated from July 1996. One seedling was selected in view of its growth habit, flower color and flowering time in December 1996. That seedling was propagated by cutting and grown in pots starting from July 1999, at Hakushu-cho, Kitakoma-gun, Yamanashi-ken, Japan. The botanical characteristics of that plant were then examined, using similar varieties 'Sunsenere' (U.S. Plant Pat. No. 12,162) and 'Midget' (unpatented) for comparison. As a result, it was concluded that this *Senecio* plant is distinguishable from any other variety, whose existence is known to us, and is uniform and stable in its characteristics. The new variety of *Senecio* plant was named 'Sunsenebare'.

In the following description, the color-coding is in accordance with The Horticultural Colour Chart of The Royal Horticultural Society, London, England (R.H.S.).

SUMMARY OF THE VARIETY

This new variety is unlike any *Senecio* commercially available known to the inventor as evidenced by the following unique combinations of characteristics.

1. Semi-dwarf, obconical plant shape having abundant branching with small leaves.
2. The capitula are single and small. The ray florets and disc floret color is vivid reddish purple (near R.H.S. 78A).
3. Blooming time is early, and flowering duration is long.
4. Low fertility.

The new variety 'Sunsenebare' differs from the similar variety 'Sunsenere' in the following points.

1. The plant of 'Sunsenebare' is more compact than that of 'Sunsenere'.
2. The capitulum diameter of 'Sunsenebare' is smaller than that of 'Sunsenere'.
3. The peduncle length of 'Sunsenebare' is shorter than that of 'Sunsenere'.
4. The blooming time of 'Sunsenebare' is earlier than that of 'Sunsenere'.

The new variety 'Sunsenebare' differs from the similar variety 'Midget' in the following points.

1. The plant size of 'Sunsenebare' is larger than that of 'Midget'.
2. The branches of 'Sunsenebare' are more numerous than that of 'Midget'.
3. The leaf of 'Sunsenebare' is smaller than that of 'Midget'.
4. The ray floret and disc floret color of 'Sunsenebare' is vivid reddish purple (near R.H.S. 78A). 'Midget' has vivid reddish purple (near R.H.S. 74A) ray florets and strong reddish purple (near R.H.S. 72A) disc florets.
5. The blooming time of 'Sunsenebare' is earlier than that of 'Midget'.
6. The flowering duration of 'Sunsenebare' is longer than that of 'Midget'.

This new variety of *Senecio* plant 'Sunsenebare' was asexually reproduced by the use of cuttings at Hakushu-cho, Kitakoma-gun, Yamanashi-ken, Japan, and the homogeneity and stability thereof were confirmed. The instant plant retains its distinctive characteristics and reproduces true to type in successive generations.

BRIEF DESCRIPTION OF THE PHOTOGRAPH

The depicted plants had been reproduced by the use of cuttings and were photographed during January 2003 while growing outdoors in 12 cm pots at an age of approximately 5 months at Yokaichi-shi, Shiga-ken, Japan.

DESCRIPTION OF THE VARIETY

Figure 1:
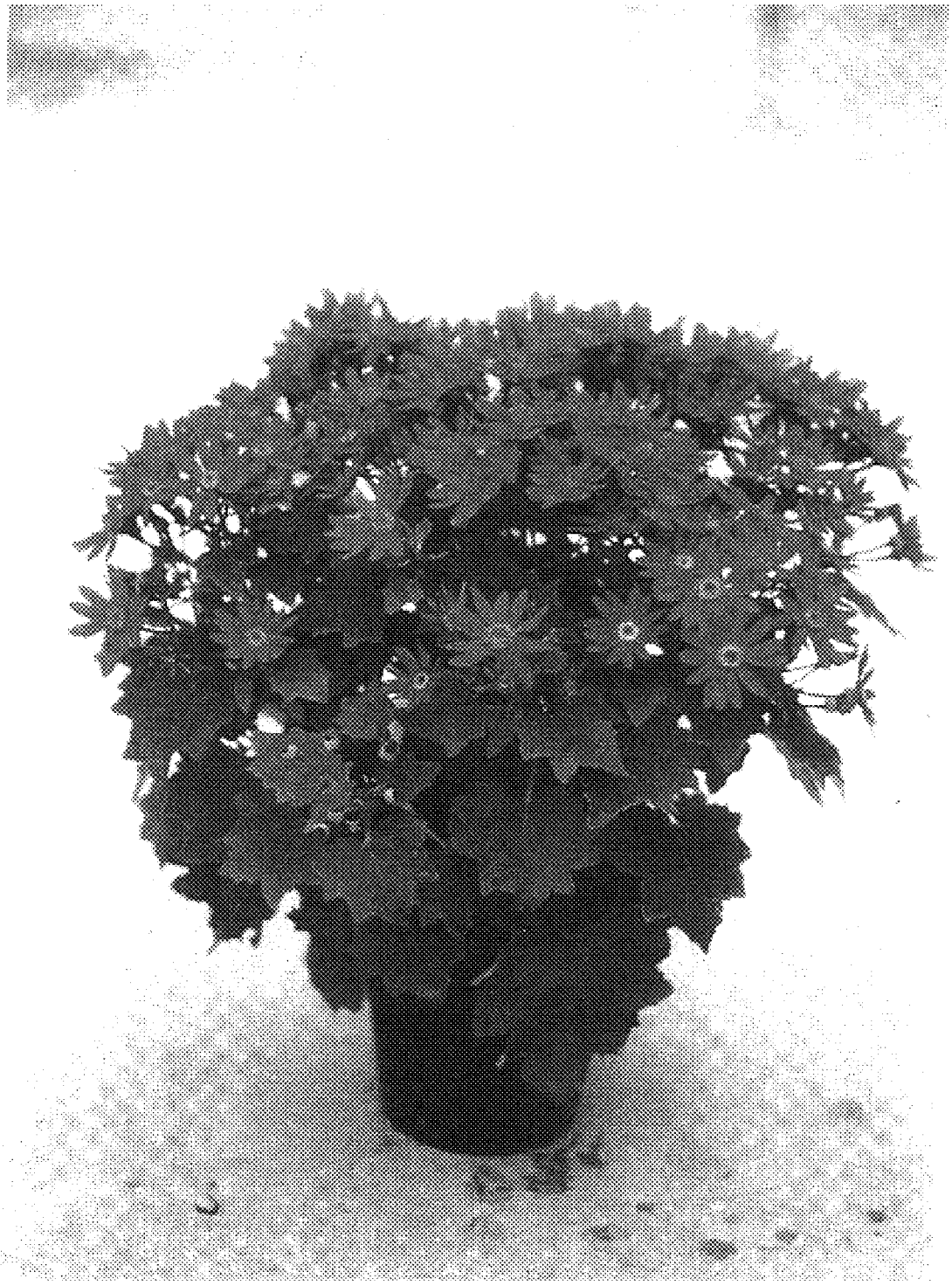
FIG. 1 illustrates a typical plant of the new variety of *Senecio* plant 'Sunsenebare', growing in a pot.
Figure 2:
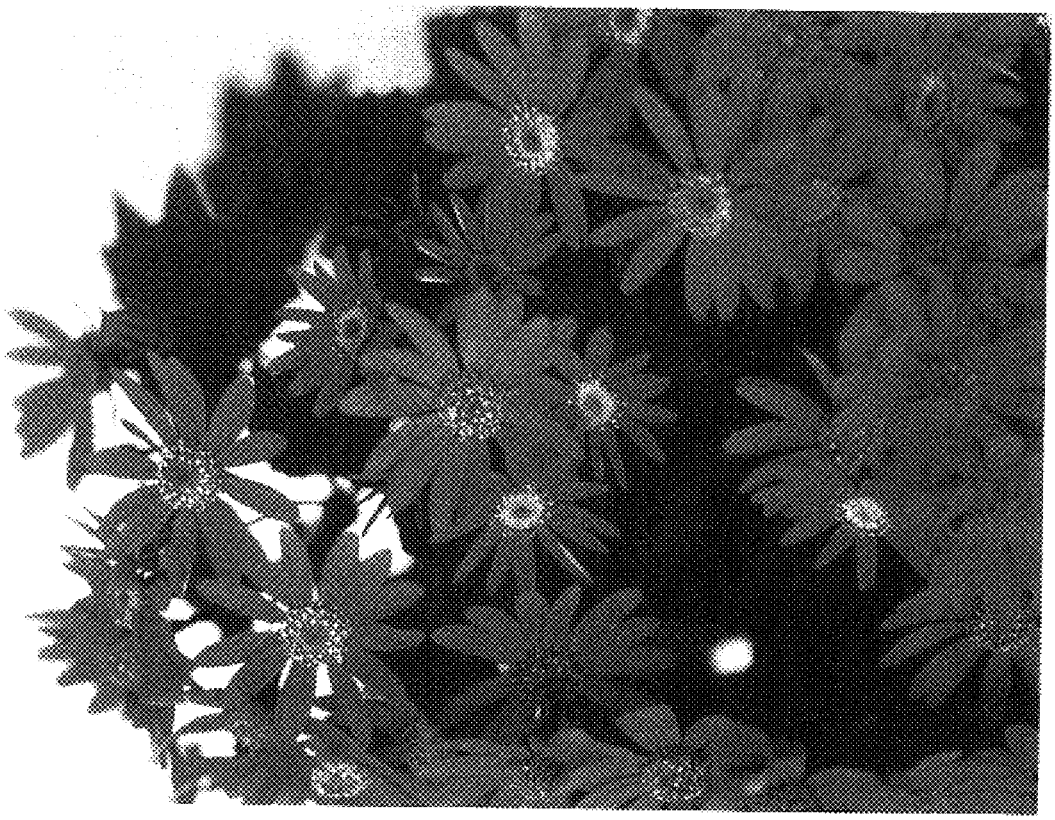
FIG. 2 illustrates a close-up view of capitula of the new variety of *Senecio* plant 'Sunsenebare'.

The botanical characteristics of the new and distinct variety of *Senecio* plant named 'Sunsenebare' are as follows, when observed during January at Yokaichi-shi, Shiga-ken, Japan, at an age of approximately 5 months.

Plant:

*Growth habit.*—Semi-dwarf, obconical.
*Height.*—Approximately 25.5 cm.
*Width.*—Approximately 19 cm.

Stem:

*Length.*—Approximately 15 cm.
*Thickness.*—Approximately 4.2 mm.
*Color.*—Near R.H.S. 144A (strong yellow green).
*Anthocyanin coloration.*—Absent.
*Number of branches.*—Abundant.
*Type of primary lateral shoot.*—Branch from every node.
*Pubescence.*—Moderate.
*Length of internode.*—Approximately 1.6 cm.

Leaf:

*Whole shape.*—Cordate.
*Leaf margin.*—Dentate, undulated.
*Apex shape.*—Obtuse.
*Base shape.*—Cordate.
*Length.*—Approximately 8.2 cm.
*Width.*—Approximately 9.3 cm.
*Diameter of petiole.*—Approximately 3.1 mm.
*Length of petiole.*—Approximately 6.7 cm.
*Color of petiole.*—Near R.H.S. 144B.
*Color of upper surface.*—Near R.H.S. 144A.
*Color of lower surface.*—Near R.H.S. 139D.
*Anthocyanin coloration of reverse surface.*—Absent.
*Pubescence of upper surface.*—Moderate.
*Pubescence of lower surface.*—Dense.
*Pattern of venation.*—Reticulate venation.
*Color of venation.*—Near R.H.S. 138B.
*Stipule.*—Absent.

Inflorescence cluster (gathering of corymbs):

*Shape of inflorescence.*—Flat.
*Diameter of inflorescence.*—Approximately 33 cm.
*Height of inflorescence.*—Approximately 19 cm.
*Capitulum.*—Transected shape of capitulum — Flat. Diameter of capitulum — Approximately 4.1 cm. Disc diameter — Approximately 0.9 cm. Color of ray floret — Upper side: near R.H.S. 78A; Lower surface — near R.H.S. N74C.
*Disc floret.*—Shape — Tubular, trumpet shape. Color (both surfaces — Near R.H.S. 78A to 77C. Length — Approximately 8.5 mm. Diameter — Approximately 1.0 mm. Margin — 5 lobed, star shape. Apex shape — Acute. Base shape — Fused. Marginal variegation — Absent.
*Ray floret.*—Length — Approximately 1.6 cm. Width — Approximately 0.5 cm. Shape — Oblong. Base shape — Obtuse. Margin — Entire. Texture — Velvety. Lengthwise warp — Flat. Shape of tip — Acute.
*Number of ray florets.*—13 (single whorl).
*Number of disc florets.*—Approximately 110.
*Diameter of pedicel.*—Approximately 1.1 mm.
*Length of pedicel.*—Approximately 2.2 cm.
*Pedicel color.*—Near R.H.S. N77C.
*Number of capitula per plant.*—Approximately 120.
*Scent.*—Present.

Bud:

*Hardiness.*—Tolerant to 0° C. However, the plant would be seriously damaged by frost, the same as other *Senecio* plants, at any temperature.
*Length.*—Approximately 6.0 mm.
*Diameter.*—Approximately 6.0 mm.
*Shape.*—Globose.
*Surface.*—Smooth.
*Color.*—Near R.H.S. 144A.

Involucre:

*Type.*—Bracts in a whorl, fused at the base, outwardly recurved.

*Length of bracts* (*separated portion*).—Approximately 2.0 mm.

*Width of bracts* (*separated portion*).—Approximately 1.0 mm.

*Number of bracts per capitulum.*—Approximately 14.

*Margin of bracts.*—Entire.

*Apex shape of bracts.*—Acute.

*Color* (*both surfaces*).—Near R.H.S. 143C.

*Anthocyanin coloration* (*both surfaces*).—Absent.

Pistil:

*Color.*—Near R.H.S. 80A.

*Number.*—1 per ray and disc floret.

*Type.*—Style branches truncate.

Stamen:

*Pollen.*—Moderate, color near R.H.S. 10A.

*Color.*—Near R.H.S. 71A (deep purplish red).

*Type.*—Synantherous. A disc floret has 5 connate anthers with separated filament. Ray floret has no stamen.

*Blooming time.*—Beginning of November to May. In Japan, plant starts flowering about 5 months after planting rooted cuttings.

*Lastingness of an individual bloom on the plant.*—Approximately 2 weeks at around 15° C.

Hardiness:

*Cold.*—Good.

*Heat.*—Good.

Resistance:

*Disease.*—Good.

*Insect.*—Good.

The new variety and *Senecio cruentus* have similar resistance to powdery mildew, leaf spot, aphid, whitefly and thrips. The new variety 'Sunsenebare' is most suitable for flower potting.

It is claimed:

1. A new variety of *Senecio* plant named 'Sunsenebare', substantially as herein illustrated and described.

* * * * *